United States Patent
Ditzel et al.

(10) Patent No.: US 8,536,369 B2
(45) Date of Patent: *Sep. 17, 2013

(54) PROCESS FOR THE CARBONYLATION OF DIMETHYL ETHER

(75) Inventors: Evert Jan Ditzel, North Humberside (GB); Andre Harmen Sijpkes, Almere (NL); John Glenn Sunley, Cottingham (GB)

(73) Assignee: BP Chemicals Limited, Middlesex (GB)

(*) Notice: Subject to any disclaimer, the term of this patent is extended or adjusted under 35 U.S.C. 154(b) by 557 days.

This patent is subject to a terminal disclaimer.

(21) Appl. No.: 12/451,004

(22) PCT Filed: Apr. 23, 2008

(86) PCT No.: PCT/GB2008/001420
§ 371 (c)(1),
(2), (4) Date: Oct. 22, 2009

(87) PCT Pub. No.: WO2008/132441
PCT Pub. Date: Nov. 6, 2008

(65) Prior Publication Data
US 2010/0121098 A1    May 13, 2010

(30) Foreign Application Priority Data
Apr. 26, 2007 (EP) .................................. 07251767

(51) Int. Cl.
*C07C 67/37* (2006.01)
(52) U.S. Cl.
USPC .......................................... 560/232; 560/241
(58) Field of Classification Search
USPC .................... 560/232, 241; 502/242, 244
See application file for complete search history.

(56) References Cited

U.S. PATENT DOCUMENTS

| | | | | |
|---|---|---|---|---|
| 5,934,072 A | * | 8/1999 | Hirota et al. | .................... 60/301 |
| 6,160,163 A | * | 12/2000 | Zoeller et al. | .................. 560/207 |
| 6,509,293 B1 | * | 1/2003 | Zoeller et al. | .................. 502/344 |
| 2003/0018212 A1 | | 1/2003 | Zoeller et al. | |
| 2006/0252959 A1 | | 11/2006 | Cheung et al. | |
| 2006/0287551 A1 | | 12/2006 | Cheung et al. | |

FOREIGN PATENT DOCUMENTS

| | | |
|---|---|---|
| WO | WO 02/102755 | 12/2002 |
| WO | WO 2006/121778 | 11/2006 |

OTHER PUBLICATIONS

Blasco, T. et al. "Carbonylation of methanol on metal-acid zeolites: evidence for a mechanism involving a multisite active center," Angew. Chem. Int. Ed. (2007) 46: 3938-3941.*
International Search Report for PCT/GB2008/001420, mailed Aug. 21, 2008.
Written Opinion of the International Searching Authority for PCT/GB2008/001420, mailed Aug. 21, 2008.
Database Abstract; Accession No. 1975-58008W & JP 50-022538, (Jul. 31, 1975); 1 page.
Cheung et al., "Site Requirements and Elementary Steps in Dimethyl Ether Carbonylation Catalyzed by Acidic Zeolites", Journal of Catalysis, vol. 245, No. 1, (Nov. 18, 2006), pp. 110-123.

* cited by examiner

*Primary Examiner* — Johann R Richter
*Assistant Examiner* — Pancham Bakshi
(74) *Attorney, Agent, or Firm* — Nixon & Vanderhye

(57) ABSTRACT

Process for producing methyl acetate by carbonylating a dimethyl ether feed with carbon monoxide under substantially anhydrous conditions in the presence of a mordenite catalyst which has been ion-exchanged or otherwise loaded with at least one of silver and copper. The mordenite is also ion-exchanged or otherwise loaded with platinum in an amount in the range 0.05 to 10 mol % relative to aluminum.

15 Claims, 1 Drawing Sheet

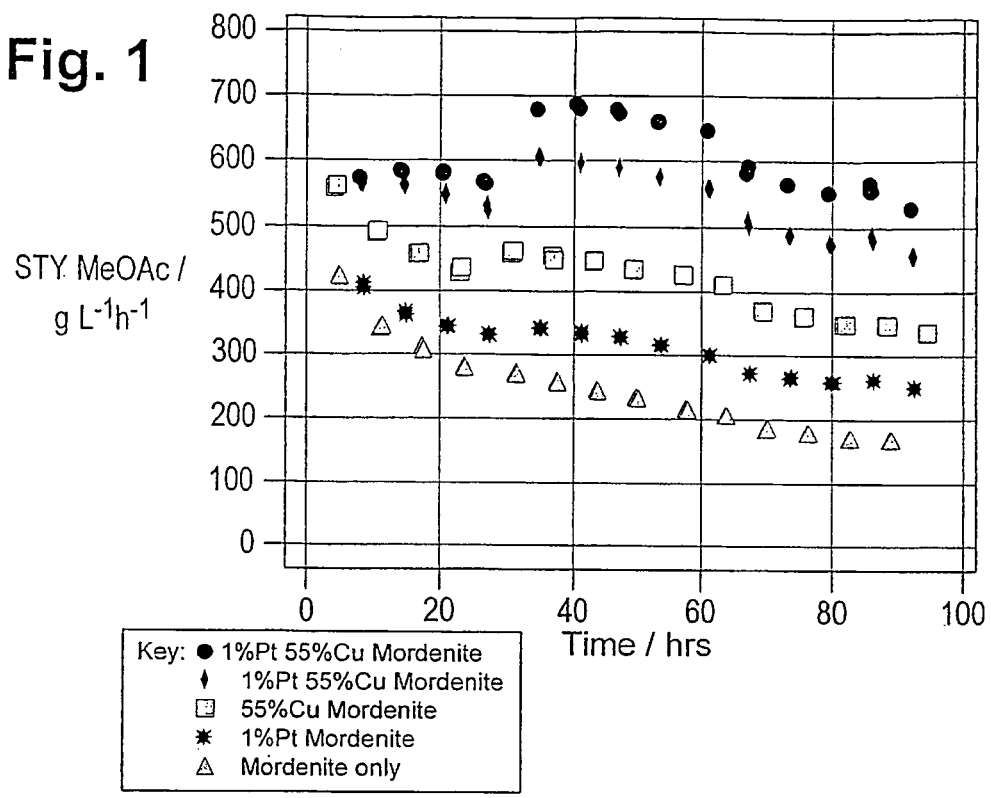
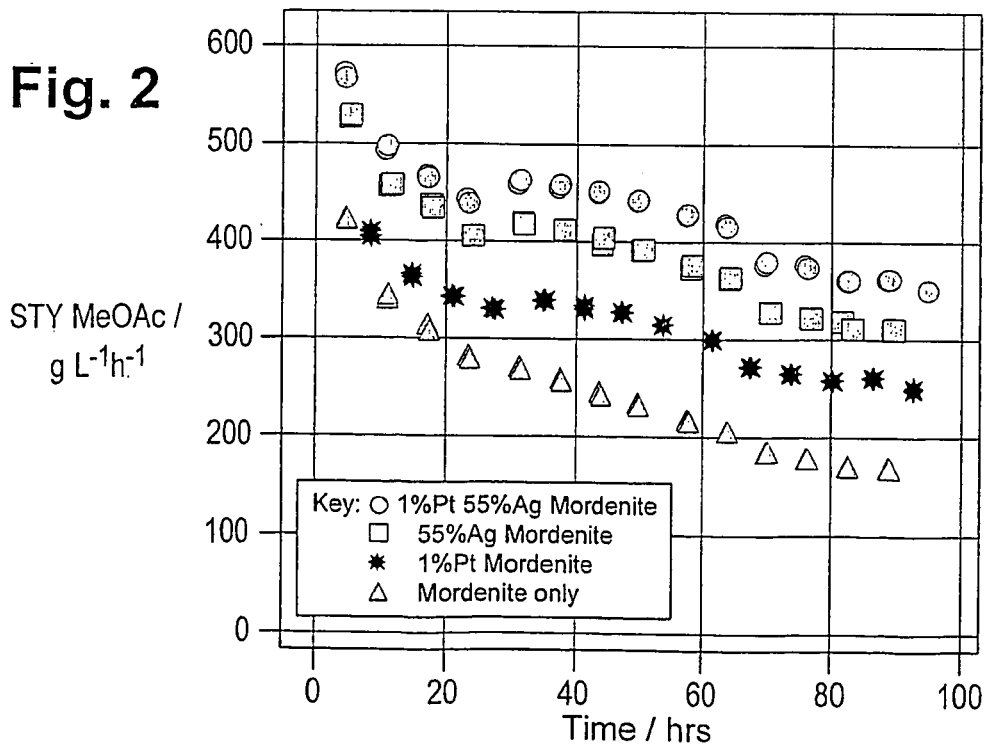

PROCESS FOR THE CARBONYLATION OF DIMETHYL ETHER

This application is the U.S. national phase of International Application No. PCT/GB2008/001420 filed 23 Apr. 2008, which designated the U.S. and claims priority to Europe Application No. 07251767.5 filed 26 Apr. 2007, the entire contents of each of which are hereby incorporated by reference.

This invention relates to a process for preparing methyl acetate by reacting dimethyl ether with carbon monoxide in the presence of a zeolite catalyst.

BACKGROUND OF THE INVENTION

Liquid phase carbonylation processes such as the carbonylation of methanol and/or reactive derivatives thereof in the presence of homogeneous catalysts to produce acetic acid are operated commercially. Gas phase carbonylation processes employing methanol and dimethyl ether using heterogeneous catalysts are also known.

EP-A-0 596 632 describes a vapour phase process for the carbonylation of methanol to produce acetic acid at high temperatures and pressures in the presence of a mordenite catalyst which has been loaded with copper, nickel, iridium, rhodium or cobalt WO 01/07393 describes a process for the catalytic conversion of a feedstock comprising carbon monoxide and hydrogen to produce at least one of an alcohol, ether and mixtures thereof and reacting carbon monoxide with the at least one of an alcohol, ether and mixtures thereof in the presence of a catalyst selected from solid super acids, heteropolyacids, clays, zeolites and molecular sieves, in the absence of a halide promoter, under conditions of temperature and pressure sufficient to produce at least one of an ester, acid, acid anhydride and mixtures thereof. However, the use of zeolites to catalyse the carbonylation reaction is not exemplified.

WO 2005/105720 describes a process for production of a carboxylic acid and/or an ester or anhydride thereof by carbonylating an aliphatic alcohol or reactive derivative thereof with carbon monoxide in the substantial absence of halogens at a temperature in the range 250-600° C. and a pressure in the range 10 to 200 bar in the presence of a mordenite catalyst which has been modified with copper, nickel, iridium, rhodium or cobalt and has as framework elements, silicon, aluminium, and at least one of gallium, boron and iron. The use of dimethyl ether as a feedstock is not exemplified.

WO 2006/121778 describes a process for the production of a lower alkyl ester of a lower aliphatic carboxylic acid by carbonylating under substantially anhydrous conditions a lower alkyl ether, such as dimethyl ether, with carbon monoxide in the presence of a mordenite or ferrierite catalyst. The use of a gallium framework modified mordenite as catalyst for the carbonylation of dimethyl ether is exemplified In view of the above-mentioned prior art, there remains the need for an improved heterogeneous gas phase process for the production of methyl acetate from dimethyl ether under substantially anhydrous conditions using a zeolite catalyst.

SUMMARY OF THE INVENTION

It has now been found that improved catalytic activity can be achieved if the carbonylation process is carried out using a copper and/or silver mordenite catalyst which has also been loaded with low levels of platinum.

Accordingly, the present invention provides a process for the production of methyl acetate which process comprises the carbonylation of a dimethyl ether feed with carbon monoxide under substantially anhydrous conditions, in the presence of a mordenite catalyst which has been ion-exchanged or otherwise loaded with at least one of silver and copper, and wherein the mordenite is also ion-exchanged or otherwise loaded with platinum in an amount in the range 0.05 to 10 mol % relative to aluminium.

The dimethyl ether used as the feed in the process of the present invention may be substantially pure dimethyl ether. In commercial practice, dimethyl ether is produced by the catalytic conversion of synthesis gas (mixtures of hydrogen and carbon monoxide) over methanol, synthesis and methanol dehydration catalysts. This catalytic conversion results in a product which is predominantly dimethyl ether but it may also contain some methanol. In the process of the present invention the dimethyl ether feed may comprise small amounts of methanol provided that the amount of methanol present in the feed is not so great as to inhibit the carbonylation of dimethyl ether to methyl acetate product. It has been found that 5 wt % or less, such as 1 wt % or less of methanol may be tolerated in the dimethyl ether feed.

Suitably, dimethyl ether is present at a concentration in the range of 0.1 to 20 mol %, such as 1.5 mol % to 20 mol %, for example, 1.5 mol % to 10 mol % and 1.5 mol % to 5 mol %, based on the total feed (including recycles).

The carbon monoxide may be substantially pure carbon monoxide, for example, carbon monoxide typically provided by suppliers of industrial gases, or it may contain impurities that do not interfere with the conversion of the dimethyl ether to methyl acetate, such as nitrogen, helium, argon, methane and/or carbon dioxide.

The carbon monoxide feed may contain hydrogen. Mixtures of hydrogen and carbon monoxide are commercially produced by the steam reforming of hydrocarbons and by the partial oxidation of hydrocarbons. Such mixtures are commonly referred to as synthesis gas. Synthesis gas comprises mainly carbon monoxide and hydrogen but may also contain smaller quantities of carbon dioxide.

Suitably, the molar ratio of carbon monoxide:hydrogen may be in the range 1:3 to 15:1, such as 1:1 to 10:1, for example, 1:1 to 4:1.

Where hydrogen is present in the process, it may be present at a partial pressure of at least 0.1 barg, such as 1 to 30 barg.

The molar ratio of carbon monoxide to dimethyl ether is suitably in the range 1:1 to 99:1, such as 2:1 to 60:1.

The catalyst used in the process of the present invention is a mordenite which has been ion-exchanged or otherwise loaded with platinum and at least one of silver and copper. The structure of mordenite is well known and defined, for example, in The *Atlas of Zeolite Framework Types* (C. Baerlocher, W. M. Meier, D. H. Olson, 5th ed. Elsevier, Amsterdam, 2001). The web-based version (http://www.iza-structure.org/databases/) is a compendium of topological and structural details about zeolites including mordenite.

Mordenite is commonly available as Na-mordenite, $NH_4$-mordenite or H-mordenite. Prior to use as a catalyst, the mordenite is ion-exchanged or otherwise loaded with platinum and one or more of silver and copper. The loading of the mordenite with these metals may be by any method such as the well-known techniques of ion-exchange, wet impregnation and incipient wetness. If the mordenite is to be ion-exchanged up to 100% of the cation-exchangable sites on the zeolite may be exchanged with the metal ions using well known techniques. It is preferred that any remaining cations in the exchanged mordenite are protons hence it is convenient to start the exchange process from the ammonium or hydrogen form.

As an alternative to ion-exchange, the ammonium or hydrogen form of the mordenite can be impregnated with a solution of the metal salts and subsequently dried. If the ammonium form is used, it is preferred to calcine the mordenite after the loading or ion-exchange with the platinum and copper/silver metals has been completed.

The metals may be loaded onto the mordenite simultaneously or sequentially. If the loading is carried out sequentially, a calcination and/or a drying step may be employed between each metal loading. After loading of the final metal component, the catalyst may be dried and/or calcined. The calcination may be carried out at high temperature, for example 500° C. Where the loading is carried out sequentially, the copper and/or silver is preferably loaded onto the zeolite prior to the loading of the platinum.

Any suitable copper, silver and platinum salts or complexes may be used for impregnation of the mordenite. Suitably, solutions of platinum (II) nitrate, copper acetate, copper (II) salts such as copper (II) nitrate and silver nitrate may be used. Other suitable platinum compounds which may be employed are $Pt(NH_3)_4(OH)_2 \cdot xH_2O$, platinum (II) acetylacetonate and $[Pt(NH_3)_4](NO_3)_2$. In general, the use of platinum complexes which contain alkali metal counter-ions such as $Pt(NO_3)_4(K^+)_2$ are not preferred, as the alkali metal counter-ions may act as a poison for the carbonylation reaction.

The metal loading in the mordenite can be expressed in terms of the fractional loading of the metal as gram atoms of metal per gram atom of aluminium in the mordenite. The metal loading can also be expressed as a mole percentage loading relative to aluminium in the mordenite through the relationship mol % Metal=(gram atoms Metal/gram atoms aluminium)×100

Thus, for example, a loading of 0.55 gram atom of copper per aluminium in the mordenite equates to a 55 mol % loading of copper relative to aluminium in the mordenite.

Each of copper and silver may be loaded in an amount in the range of 1 to 200 mol % relative to aluminium, for example, 50 to 120 mol %, such as 50 to 110 mol %, suitably, 55 to 120 mol %, such as 55 to 110 mol %. The total loading of copper and silver, may suitably be in the range 1 to 200 mol % relative to aluminium, for example, 55 to 120 mol %, such as 55 to 110 mol % or 50 to 120 mol %, such as 50 to 110 mol %.

Platinum is loaded in an amount in the range 0.05 to 10 mol % relative to aluminium such as 1 to 10 mol %, for example 1 to 5 mol %. Suitable platinum loadings are for example, 0.05 to 5 mol %, such as 0.05 to 2 mol %.

The mordenite framework, may, in addition to the silicon and aluminium framework atoms; contain additional elements, such as gallium, iron and/or boron.

For the process of the present invention it is preferred that the mordenite has a silica to alumina ratio of at least 5 but preferably less than or equal to 100, such as in the range 7 to 40, for example 10 to 30. Where the aluminium atoms have been replaced by framework modifier elements, it is preferred that the ratio of silica:$X_2O_3$ where X is a trivalent element, such as aluminium, gallium, iron and/or boron, is at least 5 and preferably less than or equal to 100, such as in the range 7 to 40, for example 10 to 30.

Where the mordenite contains additional trivalent framework elements the metal loading in the mordenite can be expressed in terms of the fractional loading of the metal as gram atoms of metal per gram atom of total trivalent elements in the mordenite. The metal loading can also be expressed as a mole percentage loading relative to total trivalent elements in the mordenite through the relationship:

mol % Metal=(gram atoms Metal/gram atoms of total trivalent elements)×100

The process is carried out under substantially anhydrous conditions, i.e. in the substantial absence of water. The carbonylation of dimethyl ether to methyl acetate does not generate water in-situ. Water has been found to inhibit the carbonylation of dimethyl ether to form methyl acetate. Thus, in the process of the present invention, water is kept as low as is feasible. To accomplish this, the dimethyl ether and carbon monoxide reactants (and catalyst) are preferably dried prior to introduction into the process. However, small amounts of water may be tolerated without adversely affecting the formation of methyl acetate. Suitably, water may be present in the dimethyl ether feed in an amount of 2.5 wt % or less, such as 0.5 wt % or less.

The process of the present invention may suitably be carried out at a temperature in the range of 100° C. to 350° C.

The process of the present invention may be carried out at a pressure in the range 1 to 100 barg, such as 10 to 100 barg.

The Gas Hourly Space Velocity (GHSV) is suitably in the range 500 to 40,000 $h^{-1}$, such as 2000 to 20,000 $h^{-1}$.

Because the carbonylation reaction is to be conducted substantially in the absence of water, it is preferred that the mordenite catalyst is dried prior to use. The catalyst may be dried, for example by heating to a temperature of 400 to 500° C.

It is preferred that the mordenite catalyst is activated immediately before use by heating the catalyst at elevated temperature for at least one hour under flowing nitrogen, carbon monoxide, hydrogen or mixtures thereof.

Preferably, the process of the present invention is carried out substantially in the absence of halides, such as iodide. By the term 'substantially' is meant that the total halide, for example, iodide content of the reactant gases (dimethyl ether and carbon monoxide) and catalyst is less than 500 ppm, preferably less than 100 ppm.

The process of the present invention is suitably carried out by passing dimethyl ether vapour and carbon monoxide gas through a fixed bed, fluidised bed or moving bed of the mordenite catalyst maintained at the desired temperature and pressure.

If desired, the dimethyl ether feed may be contacted with a bed of alumina or corundum immediately before the bed of mordenite catalyst.

The primary product of the process is methyl acetate but small amounts of acetic acid may also be produced. The methyl acetate produced by the process of the present invention can be removed in the form of a vapour and thereafter condensed to a liquid.

The methyl acetate may be recovered and sold as such or it may be forwarded to other chemical processes. Where the methyl acetate is recovered from the carbonylation reaction products, some or all of it may be hydrolysed to form acetic acid. Alternatively, the entire carbonylation reaction product may be passed to a hydrolysis stage and acetic acid separated thereafter. The hydrolysis may be carried out by known techniques such as reactive distillation in the presence of an acid catalyst.

The process may be operated as either a continuous or a batch process, preferably as a continuous process.

The invention is now illustrated with reference to the following Examples.

EXAMPLE 1

Catalyst Preparation

Preparation of H-Mordenite

Mordenite with a silica to alumina ratio of 20 (ex Südchemie) was compacted with a powtec roller compactor at 250 bar using a total of 4 cycles, then crushed and sieved to a particle size fraction of 125 to 160 microns. 2.5 g of the mordenite was then calcined in a muffle oven (oven-volume=12 L) at a temperature of 500° C. under air (air flow 1 L/min) at a ramp rate of 1° C./min to a temperature of 120° C., held at 120° C. for 180 minutes, then the temperature was increased by 1° C./min to 500° C., held at 500° C. for 180 minutes.

Preparation of Ag Loaded Mordenite

Mordenite with a silica to alumina ratio of 20 (ex Südchemie) was treated with a silver (I) nitrate solution to give a silver loading of 55 mol % relative to aluminium in the mordenite.

A solution comprising 852 µL silver (I) nitrate concentration of 4 mol/L dissolved in 3648 µL $H_2O$ was made-up and used to impregnate 5 g of the mordenite. The LOI (loss on ignition, 600° C.) of the mordenite was measured (typically 10-20%, in this case 18.03%) to account for the amount of water adsorbed on the mordenite in order to determine the amount of metal solution required to achieve the desired loading of silver. After the impregnation the mordenite was left at ambient conditions on a shaker for 1 hour. Subsequently the silver loaded mordenite was transferred to a forced convection oven (air as atmosphere) and heated to 80° C. for 20 hours. After the drying step the silver loaded mordenite was calcined in air using the following procedure: calcination in a muffle oven (oven-volume=12 L) at a temperature of 500° C. under air (air flow 1 L/min) at a ramp rate of 1° C./min to a temperature of 120° C., held at 120° C. for 180 minutes, then the temperature was increased by 1° C./min to 500° C., held at 500° C. for 180 minutes. The silver loaded mordenite was then cooled down to room temperature in the muffle oven under (dry) air flow 1 L/min. The silver loaded mordenite was then gently pushed through a 160 µm sieve and sieved to obtain particles having a size in the range 125-160 µm.

Preparation of Cu Loaded Mordenite

Mordenite with a silica to alumina ratio of 20 (ex Südchemie) was treated with a copper(II)nitrate solution, to give a copper loading of 55 mol % relative to aluminium in the mordenite.

A solution of 426 µL copper(II)nitrate of concentration of 4 mol/L dissolved in 1824 µL $H_2O$ was made-up and used to impregnate 2.5 g of the mordenite. The LOI (loss on ignition, 600° C.) of the mordenite was measured (typically 10-20%, in this case 18.03%) to account for the amount of water adsorbed on the mordenite in order to determine the amount of metal solution required to achieve the desired loading of copper. After the impregnation the mordenite was left at ambient conditions on a shaker, for 1 hour. Subsequently, the copper loaded mordenite was transferred to a forced convection oven (air as atmosphere) and heated to 80° C. for 20 hours. After the drying step the copper loaded mordenite was calcined in air using the following procedure: calcination in a muffle oven (oven-volume=12 L) at a temperature of 500° C. under air (air flow 1 L/min) at a ramp rate of 1° C./min to a temperature of 120° C., held at 120° C. for 180 minutes, then the temperature was increased by 1° C./min to 500° C., held at 500° C. for 180 minutes. The copper loaded mordenite was then cooled to room temperature in the muffle oven under (dry) air flow 1 L/min. The copper loaded mordenite was then gently pushed through a 160 µm sieve and sieved to obtain particles having a size in the range 125-160 µm.

Preparation of Pt Loaded Mordenite

Mordenite with a silica to alumina ratio of 20 (ex Südchemie) was treated with a platinum (II) nitrate solution, to give a platinum loading of 1 mol % relative to aluminium in the mordenite.

A solution of 309 µL platinum (II) nitrate of concentration of 0.1 mol/L dissolved in 1941 µL $H_2O$ was made-up and used to impregnate 2.5 g of the mordenite. The LOI (loss on ignition, 600° C.) of the mordenite was measured (typically 10-20%, in this case 18.03%) to account for the amount of water adsorbed on the mordenite in order to determine the amount of metal solution required to achieve the desired platinum loading. After the impregnation, the mordenite was left at ambient conditions on a shaker for 1 hour. Subsequently, the platinum loaded mordenite was transferred to a forced convection, oven (air as atmosphere) and heated to 80° C. for 20 hours. After the drying step the platinum loaded mordenite was calcined in air using the following procedure: calcination in a muffle oven (oven-volume=12 L) at a temperature of 500° C. under air (air flow 1 L/min) at a ramp rate of 1° C./min to a temperature of 120° C., held at 120° C. for 180 minutes, then the temperature was increased by 1° C./min to 500° C., held at 500° C. for 180 minutes. The platinum loaded mordenite was then cooled to room temperature in the muffle oven under (dry) air flow 1 L/min. The platinum loaded mordenite was then gently pushed through a 160 µm sieve and sieved to obtain particles having a size in the range 125-160 µm.

Preparation of Ag/Pt Loaded Mordenite

Mordenite with a silica to alumina ratio of 20 (ex Südchemie) was treated with a platinum (II) nitrate solution, to give a platinum loading of 1 mol % relative to aluminium in the mordenite and with a silver (I) nitrate solution, to give a silver loading of 55 mol % relative to aluminium in the mordenite. A solution comprising 309 µL platinum (II) nitrate of concentration of 0.1 mol/L and 426 µL silver (I) nitrate concentration of 4.0 mol/L dissolved in 1515 µL $H_2O$ was made-up and used to impregnate 2.5 g of the mordenite. The LOI (loss on ignition, 600° C.) of the mordenite was measured (typically 10-20%, in this case 18.03%) to account for the amount of water adsorbed on the mordenite in order to determine the amount of metal solution required to achieve the desired loadings of silver and platinum. After the impregnation the mordenite was left at ambient conditions on a shaker for 1 hour. Subsequently, the silver/platinum loaded mordenite was transferred to a forced convection oven (air as atmosphere) and heated to 80° C. for 20 hours. After the drying step the silver/platinum loaded mordenite was calcined in air using the following procedure: calcination in a muffle oven (oven-volume=12 L) at a temperature of 500° C. under air (air flow 1 L/min) at a ramp rate of 1° C./min to a temperature of 120° C., held at 120° C. for 180 minutes, then the temperature was increased by 1° C./min to 500° C., held at 500° C. for 180 minutes. The silver/platinum loaded mordenite was then cooled down to room temperature in the muffle oven under (dry) air flow 1 L/min. The silver/platinum loaded mordenite was then gently pushed through a 160 µm sieve and sieved to obtain particles having a size in the range 125-160 µm.

Preparation of Cu/Pt Loaded Mordenite

Mordenite with a silica to alumina ratio of 20 (ex Südchemie) was treated with a platinum (II) nitrate solution, to give a platinum loading of 1 mol % relative to aluminium in the mordenite and with a copper (II) nitrate solution, to give a copper loading of 55 mol % relative to aluminium in the mordenite. A solution of 309 μL platinum (II) nitrate of concentration of 0.1 mol/L, plus a solution of 426 μL copper (II) nitrate of concentration of 4.0 mol/L dissolved in 1515 μL $H_2O$ was made-up and used to impregnate 2.5 g of the mordenite. The LOI (loss on ignition, 600° C.) of the mordenite was measured (typically 10-20%, in this case 18.03%) to account for the amount of water adsorbed on the mordenite in order to determine the amount of metal solution required to achieve the desired loadings of copper and platinum. After the impregnation the mordenite was left at ambient conditions on a shaker for 1 hour. Subsequently, the copper/platinum loaded mordenite was transferred to a forced convection oven (air as atmosphere) and heated to 80° C. for 20 hours. After the drying step the copper/platinum loaded mordenite was calcined in air using the following procedure: calcination in a muffle oven (oven-volume=12 L) at a temperature of 500° C. under air (air flow 1 L/min) at a ramp rate of 1° C./min to a temperature of 120° C., held at 120° C. for 180 minutes, then the temperature was increased by 1° C./min to 500° C., held at 500° C. for 180 minutes. The copper/platinum loaded mordenite was then cooled to room temperature in the muffle oven under (dry) air flow 1 L/min. The copper/platinum loaded mordenite was then gently pushed through a 160 μm sieve and sieved to obtain particles having a size in the range 125-160 μm.

Carbonylation of Dimethyl Ether

Each of the catalysts, H-mordenite, Cu-mordenite, Ag-mordenite, Pt/Cu mordenite and Pt/Ag mordenite, prepared as described above was used to catalyse the carbonylation of dimethyl ether using the following experimental procedure.

The carbonylation reactions were carried out in a pressure flow reactor unit consisting of 16 identical reactors of the type described in for example, WO 2005063372. Prior to the loading of a catalyst sample into the reactor, a 5 cm (approx.) bed of steatite of sieve fraction of 100-350 μm was placed in the respective catalyst sample holder. A 5 cm (approx.) zone of corundum of sieve fraction of 125-160 μm was placed on top of the steatit bed. A 1 ml sample of a catalyst was placed on top of the corundum bed. The catalyst sample was covered by approximately 5 cm corundum zone (inner diameter of the reactor used for the test is 3.6 mm) of a particle size of 125-160 μm. A 5 cm (approx.) zone of steatite of sieve fraction of 100-350 μm was placed on top of the corundum bed. Every zone was compacted via hitting or vibrating to get a stable bed and a defined starting height of the catalyst zone. The catalyst sample was then pressurised to the desired reaction pressure of 45 bar with CO at a flow rate of 4 L/h. The catalyst was then heated at 0.5 deg. C./min to a holding temperature of 220° C., where it was held for a dwell time of 3 hours. Subsequently the temperature was ramped to 300° C. at 0.5 deg. C./min, again followed by a dwell time of 3 hours. At this point catalyst activation was considered complete and the gas feed was switched to a mixture of carbon monoxide and hydrogen with a $CO/H_2$ ratio of 4 at a flow rate of 4 L/h, while dimethylether (DME) was fed at 0.168 L/h, 0.352 L/h and 0.536 L/h respectively as a vapour, to obtain a $CO/H_2/$DME ratio in the total feed of 76.6/19.2/4.2 from 0 to 28 h, 73/18.2/8.8 from 28 to 54 hrs and 69.3/17.3/13.4 from 54 to 95 hrs on a molar basis. Therefore the catalysts were tested at a GHSV of 4000 $h^{-1}$ with regard to the total amount of feedgas. In addition, $N_2$ was introduced at a variable rate of 0-50 ml/min to equalise the pressure swings between the 16 reactor exits. The exit stream from the test reactor was passed to a gas chromatograph to determine the concentration of reactants and carbonylation products.

BRIEF DESCRIPTION OF THE DRAWINGS

The results of the carbonylation experiments are shown in FIGS. 1 and 2.

FIG. 1 depicts the STY to methyl acetate in g $L^{-1}$ $h^{-1}$ versus time in hours for the catalysts H-mordenite, Cu-mordenite and Pt/Cu-mordenite.

FIG. 2 depicts the STY to methyl acetate in g $L^{-1}$ $h^{-1}$ versus time in hours for the catalysts H-mordenite, Ag-mordenite and Pt/Ag-mordenite.

FIGS. 1 and 2 show that the Cu-mordenite and Ag-mordenite catalysts containing platinum provide superior STY's compared to the Cu-mordenite and Ag-mordenite catalysts which do not contain platinum.

EXAMPLE 2

Catalyst Preparation

Preparation of Cu Loaded Mordenite (Catalyst A)

H-Mordenite (40 g) with a silica to alumina ratio of 20 (ex Süd Chemie) was weighed into a 500 mL round bottomed flask together with 6.43 g of copper(II)nitrate hemipentahydrate (98% ACS) and a stirrer bar. Sufficient deionised water (ca. 100 mL) was then added to the flask until a thick slurry was obtained. The top of the flask was then loosely covered and the flask left to stir overnight. The mordenite was then dried under reduced vacuum using a rotary evaporator before being dried in an oven at 100° C. for 12 hours. The mordenite was then calcined in a muffle oven (oven volume=18 L) under a static atmosphere of air. The temperature was increased from room temperature to 500° C. at a ramp rate of 5° C./min and then held at this temperature for 24 hours. The mordenite was then compacted at 12 tonnes in a 33 mm die set using a Specac Press, and then crushed and sieved to a particle size fraction of 212 to 335 microns. The mordenite had a copper loading of 55 mol % relative to aluminium.

Preparation of Cu/Pt Loaded Mordenite (Catalyst B)

3 grams of the Catalyst A as prepared above was taken in the powder form before pressing and sieving. To this was added 298 micro liters of a solution containing 0.05 grams of platinum (II) nitrate per ml of water. Additional water (to make the total amount of solution added up to ca. 3 ml) was added at the same time and the resultant slurry agitated on a roller bench for at least 1 hour to ensure thorough mixing. The copper loaded mordenite was then dried at 50° C. for at least 16 hours, then at 110° C. for 4 hours before being calcined in a muffle furnace under a static atmosphere of air. The temperature for calcination was increased from room temperature to 500° C. at a rate of 2° C./min. and then held at this temperature for 2 hours. The mordenite was then compacted at 12 tonnes in a 33 mm die set using a Specac Press, and then crushed and sieved to a particle size fraction of 212 to 335 microns. The mordenite had copper and platinum loadings of 55 mol % and 1 mol % relative to aluminium respectively.

Preparation of Cu/Pt-Mordenite (Catalyst C)

A mordenite having 55 mol % copper and 10 mol % platinum relative to aluminium was prepared as for Catalyst B above except that the amount of the solution containing 0.05 grams of platinum (II) nitrate per ml of water used was 2886 microliters instead of 298 microliters.

Carbonylation of Dimethyl Ether

Each of Catalysts A, B and C was used to catalyse the carbonylation of dimethyl ether using the following experimental procedure.

The carbonylation reactions were carried out in a pressure flow reactor unit consisting of 60 identical parallel isothermal co-current tubular reactors of the type described in, for example, WO2006107187. The reactors were arranged in 4 blocks of 15 reactors, each block having an independent temperature control. Into each reactor tube 50 micro liters of catalyst (designed to give a GHSV corresponding to 4000 $hr^{-1}$ respectively) was loaded onto a metal sinter having a pore size of 20 micrometers. All catalyst samples were heated at a ramp rate of 5° C./min. to 100° C. at atmospheric pressure under 98.6 mol % $N_2$ and 1.4 mol % He at a flow rate of 3.4 ml/min, and held at this temperature for 1 hour. The reactor was then pressurised to 30 barg with 98.6 mol % $N_2$ and 1.4 mol % He and the system held at this condition for 1 hour. The gas feed was then changed from the $N_2$ and helium mix to a mixture comprising 63.1 mol % carbon monoxide, 15.8 mol % hydrogen, 19.7 mol % nitrogen and 1.4 mol % helium at a gas flow rate of 3.4 ml/min, and the reactors were heated at a ramp rate 3° C./min. to a temperature of 300° C. The system was then held at this condition for 3 hours and 10 minutes. At this point catalyst activation is considered complete, and the gas feed was changed to a mixture comprising 63.1 mol % carbon monoxide, 15.8 mol % hydrogen, 14.8 mol % nitrogen, 1.4 mol % helium and 4.9 mol % dimethyl ether at a gas flow rate of 3.4 ml/min. The reaction was allowed to continue for ca. 112 hours. The exit stream from the reactor was passed to two gas Chromatographs. One of these was a Varian 4900 micro GC with three columns (Molecular sieve 5A, Porapak® Q, and CP-Wax-52) each quipped with a thermal conductivity detector. The other was an Interscience Trace GC with two columns (CP-Sil 5 and CP-Wax 52) each equipped with a flame ionisation detector. Data was averaged over the time period from 92.2 to 102.2 hours.

The results of the carbonylation experiments are given in Table 1 below.

TABLE 1

| Catalyst | Acetyls STY (g/l/hr) |
|---|---|
| Catalyst A (Cu mordenite) | 86 |
| Catalyst B (Cu 1% Pt mordenite) | 201 |
| Catalyst C (Cu 10% Pt mordenite) | 216 |

$STY_{acetyls}$ is defined as the STY for the production of AcOH plus the STY for the production of MeOAc multiplied by $MW_{AcOH}/MW_{MeOAc}$.

The invention claimed is:

1. A process for the production of methyl acetate which process comprises carbonylating a dimethyl ether feed with carbon monoxide under substantially anhydrous conditions, in the presence of a mordenite catalyst which has been ion-exchanged or otherwise loaded with at least one of silver and copper, and wherein the mordenite is also ion-exchanged or otherwise loaded with platinum in an amount in the range 0.05 to 10 mol % relative to aluminum.

2. A process according to claim 1 wherein the platinum loading is in the range 1 to 10 mol % relative to aluminum.

3. A process according to claim 2 wherein the platinum loading is in the range 1 to 5 mol % relative to aluminum.

4. A process according to claim 1 wherein copper is loaded in an amount in the range 1 to 200 mol % relative to aluminum.

5. A process according to claim 4 wherein the copper loading is in the range 55 to 120 mol % relative to aluminum.

6. A process according to claim 1 wherein silver is loaded in an amount in the range 1 to 200 mol % relative to aluminum.

7. A process according to claim 6 wherein silver is loaded in an amount in the range 55 to 120 mol % relative to aluminum.

8. A process according to claim 1 wherein the total loading of copper and silver is in the range 1 to 200 mol % relative to aluminum.

9. A process according to claim 1 wherein the carbonylation is carried out in the presence of hydrogen.

10. A process according to claim 1 wherein the carbonylation is carried out at a temperature in the range 100 to 350° C.

11. A process according to claim 1 wherein the carbonylation is carried out at a total pressure in the range 1 to 100 barg.

12. A process according to claim 1 wherein at least some of the methyl acetate product is hydrolyzed to acetic acid.

13. A process according to claim 1 wherein the carbonylation is carried out in the presence of hydrogen and a mordenite which has been ion-exchanged or otherwise loaded with at least one of silver and copper in an amount in the range 50 to 120 mol % relative to aluminum and ion-exchanged or otherwise loaded with platinum in an amount in the range 1 to 10 mol % relative to aluminum.

14. A process according to claim 1 wherein said catalyst is prepared by simultaneously ion-exchanging or impregnating the ammonium or hydrogen form of mordenite with platinum and at least one of silver and copper, drying and/or calcining the impregnated/ion-exchanged mordenite and wherein the catalyst comprises platinum in an amount 0.05 to 10 mol % relative to aluminum.

15. A process according to claim 1 wherein said catalyst is prepared by ion-exchanging or impregnating the ammonium or hydrogen form of mordenite with at least one of silver and copper, drying and/or calcining the impregnated/ion-exchanged mordenite to obtain a copper and/or silver loaded mordenite and subsequently ion-exchanging or impregnating the copper and/or silver loaded mordenite with platinum and wherein the catalyst comprises platinum in an amount 0.05 to 10 mol % relative to aluminum.

* * * * *